(12) United States Patent
Adler et al.

(10) Patent No.: US 11,605,452 B2
(45) Date of Patent: Mar. 14, 2023

(54) RADIOTHERAPY TREATMENT PLAN OPTIMIZATION USING MACHINE LEARNING

(71) Applicant: Elekta AB (publ), Stockholm (SE)

(72) Inventors: Jonas Anders Adler, Stockholm (SE); Jens Olof Sjölund, Stockholm (SE)

(73) Assignee: Elekta AB (publ), Stockholm (SE)

( * ) Notice: Subject to any disclaimer, the term of this patent is extended or adjusted under 35 U.S.C. 154(b) by 274 days.

(21) Appl. No.: 16/512,972

(22) Filed: Jul. 16, 2019

(65) Prior Publication Data

US 2021/0020297 A1 Jan. 21, 2021

(51) Int. Cl.
*G16H 20/40* (2018.01)
*G06N 3/08* (2023.01)

(52) U.S. Cl.
CPC ............... *G16H 20/40* (2018.01); *G06N 3/08* (2013.01)

(58) Field of Classification Search
CPC .. G16H 20/40; G06N 3/08; A61N 2005/1041; A61N 2005/1035; A61N 5/1031
See application file for complete search history.

(56) References Cited

U.S. PATENT DOCUMENTS

| | | | |
|---|---|---|---|
| 10,395,772 B1 * | 8/2019 | Lucas | G06V 30/19013 |
| 11,367,520 B2 | 6/2022 | Sjölund | |
| 2004/0165696 A1 * | 8/2004 | Lee | G16H 30/20 |
| | | | 378/65 |
| 2006/0256915 A1 * | 11/2006 | Otto | A61N 5/1031 |
| | | | 378/65 |
| 2012/0059779 A1 * | 3/2012 | Syed | G16H 50/30 |
| | | | 706/12 |
| 2017/0177812 A1 * | 6/2017 | Sjolund | G06N 20/00 |

(Continued)

FOREIGN PATENT DOCUMENTS

| | | |
|---|---|---|
| CN | 114375216 A | 4/2022 |
| CN | 114401768 A | 4/2022 |

(Continued)

OTHER PUBLICATIONS

"U.S. Appl. No. 16/512,962, Non Final Office Action dated Apr. 13, 2021", 28 pgs.

(Continued)

*Primary Examiner* — Jason S Tiedeman
*Assistant Examiner* — Liza Tony Kanaan
(74) *Attorney, Agent, or Firm* — Schwegman Lundberg & Woessner, P.A.

(57) ABSTRACT

Techniques for solving a radiotherapy treatment plan optimization problem are provided. The techniques include receiving a radiotherapy treatment plan optimization problem; processing the radiotherapy treatment plan optimization problem with a machine learning model to estimate one or more optimization variables of the radiotherapy treatment plan optimization problem, wherein the machine learning model is trained to establish a relationship between the one or more optimization variables and parameters of a plurality of training radiotherapy treatment plan optimization problems; and generating a solution to the radiotherapy treatment plan optimization problem based on the estimated one or more optimization variables of the radiotherapy treatment plan optimization problem.

21 Claims, 7 Drawing Sheets

(56) References Cited

U.S. PATENT DOCUMENTS

| | | | |
|---|---|---|---|
| 2018/0221685 A1* | 8/2018 | Eriksson | G16H 50/20 |
| 2018/0315188 A1* | 11/2018 | Tegzes | G06T 7/11 |
| 2019/0074079 A1* | 3/2019 | Zankowski | A61N 5/1039 |
| 2019/0209867 A1* | 7/2019 | Sun | A61N 5/1039 |
| 2019/0333623 A1 | 10/2019 | Hibbard | |
| 2020/0104695 A1 | 4/2020 | Laaksonen et al. | |
| 2020/0169085 A1 | 5/2020 | Becher et al. | |
| 2020/0261744 A1 | 8/2020 | Kumar et al. | |
| 2020/0289847 A1 | 9/2020 | Sjölund et al. | |
| 2021/0020296 A1 | 1/2021 | Sjölund | |
| 2021/0158929 A1 | 5/2021 | Sjolund | |

FOREIGN PATENT DOCUMENTS

| | | | | |
|---|---|---|---|---|
| WO | WO-2015103184 A1 | | 7/2015 | |
| WO | WO-2019027924 A1 | | 2/2019 | |
| WO | WO-2019084547 A1 | * | 5/2019 | G01N 30/72 |
| WO | 2021009056 | | 1/2021 | |
| WO | 2021009058 | | 1/2021 | |

OTHER PUBLICATIONS

"International Application Serial No. PCT EP2020 069588, International Search Report dated Oct. 14, 2020", 5 pgs.

"International Application Serial No. PCT EP2020 069588, Written Opinion dated Oct. 14, 2020", 6 pgs.

"International Application Serial No. PCT EP2020 069585, International Search Report dated Oct. 7, 2020", 5 pgs.

"International Application Serial No. PCT EP2020 069585, Written Opinion dated Oct. 7, 2020", 6 pgs.

Banert, Sebastian, "Data-driven nonsmooth optimization", SIAM Journal on Optimization 30.1, (2020), 102-131.

Fine, Shai, "Efficient SVM training using low-rank kernel representations", Journal of Machine Learning Research 2. Dec. 2001, 243-264.

Garnett, R., "Lecture 11: Bayesian Quadrature", University Lecture, [Online]. Retrieved from the Internet: https:www.cse.wustl.edu ~garnett cse515t spring_2017 files lecture_notes 11.pdf, (2018), 4 pgs.

Provost, Serge B., "The exact distribution of indefinite quadratic forms in noncentral normal vectors", Annals of the Institute of Statistical Mathematics 48.2, (1996), 381-394.

Rodriguez-Lujan, Irene, "Quadratic programming feature selection", Journal of Machine Learning Research, (Apr. 2010), 26 pgs.

Sjolund, Jens, "A linear programming approach to inverse planning in Gamma Knife radiosurgery", Medical physics 46.4, (2019), 1533-1544.

Zaheer, Manzil, "Deep sets", Advances in neural information processing systems, (2017), 11 pgs.

"U.S. Appl. No. 16/512,962, Response filed Jul. 13, 2021 to Non-Final Office Action dated Apr. 13, 2021", 18 pages.

"U.S. Appl. No. 16/512,962, Final Office Action dated Sep. 28, 2021", 30 pages.

"U.S. Appl. No. 16/512,962, Response filed Nov. 29, 2021 to Final Office Action dated Sep. 28, 2021", 14 pgs.

"U.S. Appl. No. 16/512,962, Advisory Action dated Jan. 10, 2022", 4 pgs.

"U.S. Appl. No. 16/512,962, Examiner Interview Summary dated Jan. 18, 2022", 3 pgs.

"U.S. Appl. No. 16/512,962, Response filed Jan. 27, 2022 to Advisory Action dated Jan. 10, 2022", 15 pgs.

"International Application Serial No. PCT EP2020 069588, International Preliminary Report on Patentability dated Jan. 27, 2022", 8 pgs.

"International Application Serial No. PCT EP2020 069585, International Preliminary Report on Patentability dated Jan. 27, 2022", 8 pgs.

"U.S. Appl. No. 16/512,962, Notice of Allowance dated Mar. 4, 2022", 10 pgs.

"U.S. Appl. No. 16/512,962, Amendment under CFR 1.312 filed Apr. 7, 2022", 3 pgs.

"U.S. Appl. No. 16/512,962, PTO Response to Rule 312 Communication dated Apr. 19, 2022", 2 pgs.

"International Application Serial No. PCT/EP2022/052412, International Search Report dated May 6, 2022", 5 pgs.

"International Application Serial No. PCT/EP2022/052412, Written Opinion dated May 6, 2022", 6 pgs.

"European Application Serial No. 20739661.5, Response to Communication pursuant to Rules 161 and 162 filed Jul. 18, 2022", 16 pgs.

"European Application Serial No. 20739662.3, Response to Communication pursuant to Rules 161 and 162 filed Aug. 24, 2022", 5 pgs.

* cited by examiner

RADIOTHERAPY TREATMENT PLAN OPTIMIZATION USING MACHINE LEARNING

TECHNICAL FIELD

This disclosure relates generally to radiation therapy or radiotherapy optimization problems.

BACKGROUND

Radiotherapy is used to treat cancers and other ailments in mammalian (e.g., human and animal) tissue. The direction and shape of the radiation beam should be accurately controlled to ensure the tumor receives the prescribed radiation, and the placement of the beam should be such as to minimize damage to the surrounding healthy tissue (often called the organ(s) at risk (OARs)). Treatment planning can be used to control radiation beam parameters, and a radiotherapy device effectuates a treatment by delivering a spatially varying dose distribution to the patient.

Traditionally, for each patient, a radiation therapy treatment plan ("treatment plan") may be created using an optimization technique based on clinical and dosimetric objectives and constraints (e.g., the maximum, minimum, and mean doses to the tumor and critical organs). The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH) objectives), taking into account their individual importance (e.g., weighting) in order to produce a treatment plan which is clinically acceptable. This task can be a time-consuming, trial-and-error process that is complicated by the various OARs, because as the number of OARs increases (e.g., 21 are commonly segmented in a head-and-neck treatment), so does the complexity of the process. OARs distant from a tumor may be easily spared from radiation, while OARs close to or overlapping a target tumor may be difficult to spare.

Segmentation may be performed to identify the OARs and the area to be treated (for example, a planning target volume (PTV)). After segmentation, a dose plan may be created for the patient indicating the desirable amount of radiation to be received by the, one or more, PTV (e.g., target) and/or the OARs. A PTV may have an irregular volume and may be unique as to its size, shape, and position. A treatment plan can be calculated after optimizing a large number of plan parameters to ensure that enough dose is provided to the PTV(s) while as low a dose as possible is provided to surrounding healthy tissue. Therefore, a radiation therapy treatment plan may be determined by balancing efficient control of the dose to treat the tumor against sparing any OAR. Typically, the quality of a radiation treatment plan may depend upon the level of experience of the planner. Further complications may be caused by anatomical variations between patients.

OVERVIEW

In some embodiments, a computer-implemented method, non-transitory computer readable medium, and a system comprising a memory and processor are provided for solving a radiotherapy treatment plan optimization problem by: receiving, by processor circuitry, a radiotherapy treatment plan optimization problem; processing, by the processor circuitry, the radiotherapy treatment plan optimization problem with a machine learning model to estimate one or more optimization variables of the radiotherapy treatment plan optimization problem, wherein the machine learning model is trained to establish a relationship between the one or more optimization variables and parameters of a plurality of training radiotherapy treatment plan optimization problems, wherein the machine learning model includes a deep neural network; and generating, by the processor circuitry, a solution to the radiotherapy treatment plan optimization problem based on the estimated one or more optimization variables of the radiotherapy treatment plan optimization problem, wherein the solution comprises at least one of radiotherapy device parameters, fluence maps, isocenter locations, beam-angles or beam-on times.

In some implementations, the machine learning model comprises one or more intermediate estimated optimization variables used in a subsequent iteration of the machine learning model.

In some implementations, processing the radiotherapy treatment plan optimization problem is performed by: processing the radiotherapy treatment plan optimization problem with the machine learning model to estimate one or more initial optimization variables; and solving the radiotherapy treatment plan optimization problem starting from the one or more initial optimization variables using a different learned or non-learned optimization process.

In some implementations, the non-learned optimization process includes at least one of a simplex method, an interior point method, a Newton method, a quasi-Newton method, a Gauss-Newton method, a Levenberg-Marquardt method, a linear least-squares method, a gradient descent method, a projected gradient method, a conjugate gradient method, an augmented Lagrangian method, a Nelder-Mead method, a branch and bound method, a cutting plane method, simulated annealing, or sequential quadratic programming.

In some implementations, the plurality of training radiotherapy treatment plan optimization problems includes at least one of: optimization problems derived from previous radiotherapy treatment plans; or synthetically generated problems.

In some implementations, the radiotherapy treatment plan optimization problem comprises at least one of images of a patient or patient volume, a segmentation of the patient volume, a dose kernel, a dose volume histogram constraint, or a dose constraint.

In some implementations, the radiotherapy treatment plan optimization problem is a constrained optimization problem and the computer-implemented method, non-transitory computer readable medium, and system are further provided for converting the radiotherapy treatment plan optimization problem to an unconstrained optimization problem based on a merit function; and processing the converted radiotherapy treatment plan optimization problem with the machine learning model to estimate the one or more optimization variables.

In some implementations, processing the radiotherapy treatment plan optimization problem with the machine learning model to estimate the one or more optimization variables is performed by: selecting a first subset of constraints of the radiotherapy treatment plan optimization problem; performing a first iteration of processing the radiotherapy treatment plan optimization problem with the machine learning model to generate a first estimate of the one or more optimization variables based on the selected first subset of the constraints; selecting a second subset of constraints of the radiotherapy treatment plan optimization problem; and performing a second iteration of processing the radiotherapy treatment plan optimization problem with the machine learning model to generate a second estimate of the one or more optimization variables based on the selected second subset of the constraints.

In some implementations, performing one or more additional iterations comprises selecting subsets of constraints and processing the radiotherapy treatment plan optimization problem with the machine learning model.

In some implementations, the first and second subsets of constraints are selected randomly.

In some embodiments, a computer-implemented method, non-transitory computer readable medium, and a system comprising a memory and processor are provided for training a machine learning model to solve a radiotherapy treatment plan optimization problem by: receiving, by processor circuitry, a plurality of training radiotherapy treatment plan optimization problems; and training the machine learning model to generate an estimate of one or more optimization variables of a radiotherapy treatment plan optimization problem by establishing a relationship between the one or more optimization variables and parameters of the plurality of training radiotherapy treatment plan optimization problems.

In some implementations, the machine learning model is trained in a supervised approach based on a plurality of solutions to the plurality of the training radiotherapy treatment plan optimization problems.

In some implementations, the machine learning model is trained in the supervised approach iteratively, in which an intermediate output of one training iteration of the machine learning model comprising intermediate estimated optimization variables is used in a subsequent training iteration of the machine learning model.

In some implementations, the plurality of training radiotherapy treatment plan optimization problems includes constrained optimization problems, and the computer-implemented method, non-transitory computer readable medium, and the system further perform: converting the plurality of training radiotherapy treatment plan optimization problems to unconstrained optimization problems based on a merit function; and training the machine learning model based on the converted radiotherapy treatment plan optimization problems.

In some implementations, the machine learning model is trained in an unsupervised approach.

The above overview is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
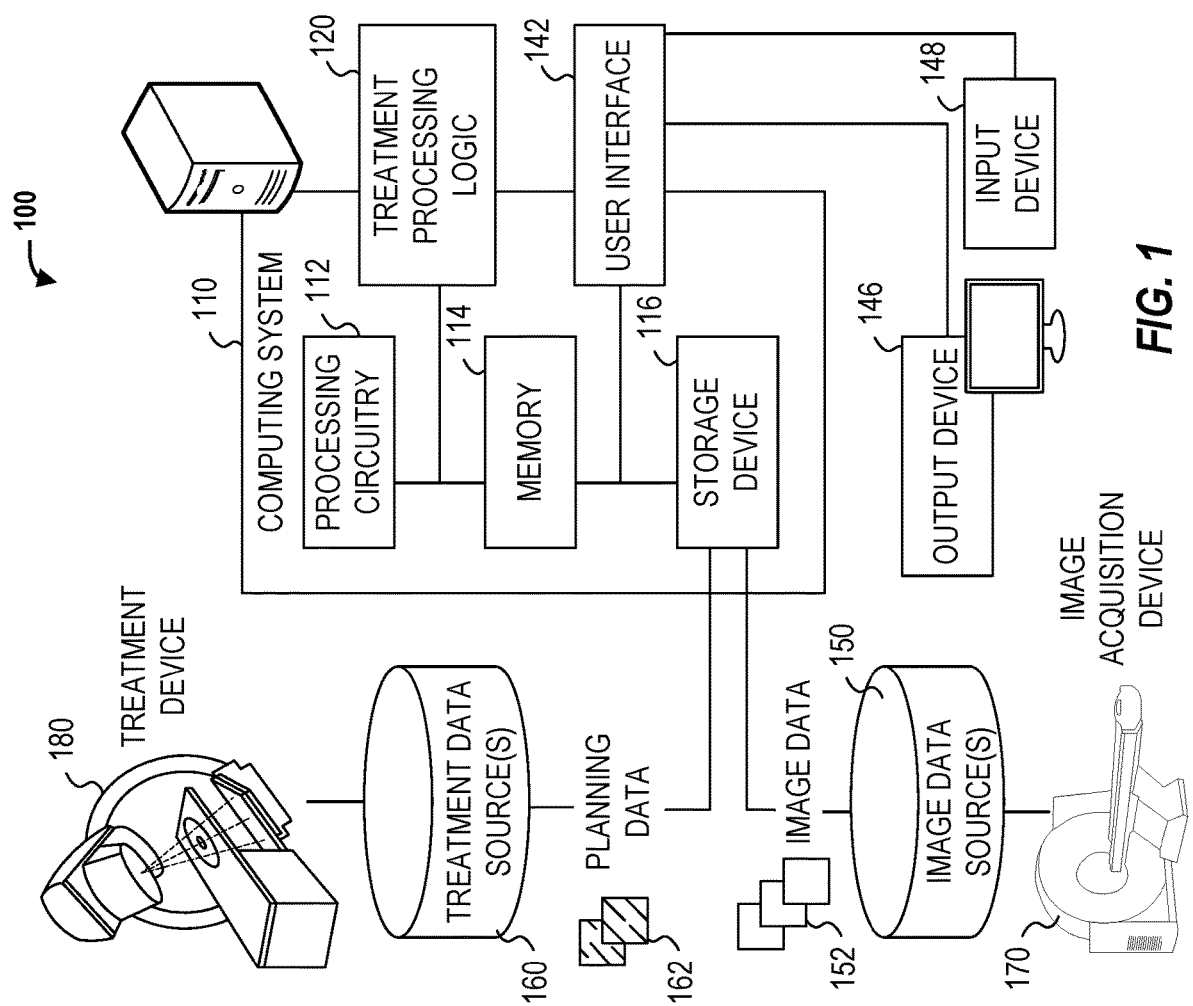
FIG. 1 illustrates an exemplary radiotherapy system adapted for performing treatment plan generation processing, according to some examples.

The present disclosure includes various techniques to generate radiotherapy treatment plans by using a machine learning (ML) model to estimate one or more optimization variables of a radiotherapy treatment plan optimization problem, which can then be used to solve the radiotherapy treatment plan optimization problem. The technical benefits include reduced computing processing times to generate radiotherapy treatment plans and solving radiotherapy treatment plan optimization problems and accompanying improvements in processing, memory, and network resources used to generate radiotherapy treatment plans and solve radiotherapy treatment plan optimization problems. These radiotherapy treatment plans may be applicable to a variety of medical treatment and diagnostic settings or radiotherapy treatment equipment and devices. Accordingly, in addition to these technical benefits, the present techniques may also result in many apparent medical treatment benefits (including improved accuracy of radiotherapy treatment, reduced exposure to unintended radiation, and the like).

Radiotherapy is one of the primary methods for treating cancer and is recommended for over 50% of all cancer patients. Treatment plans are created through a complex design process involving a mathematical optimization problem that captures the desirable characteristics of the dose delivery—typically requiring a sufficiently high dose to the target while minimizing the dose to healthy tissue. The overall structure of the optimization problem is the same for most forms of radiotherapy, including linac-based treatments (3D-CRT, IMRT, VMAT), proton treatments, Gamma Knife radiosurgery, and brachytherapy. The end result is the radiotherapy device configuration (e.g., control points) required to deliver the dose distribution.

Current planning software typically solve the minimization problem using standard mathematical optimization methods. These can be slow, causing unnecessary waiting for patients and clinicians. Future applications utilizing real-time imaging could even require real-time treatment planning, which cannot be performed using conventional optimization problem solvers.

The disclosed techniques address these challenges and increase the speed and efficiency at which radiotherapy treatment plan optimization problems are solved by leveraging a ML model or parameterized methods. Particularly, the ML model is used to estimate one or more optimization variables of a given radiotherapy treatment plan optimization problem, which simplifies and allows the radiotherapy treatment plan optimization problem to be solved much faster using the estimated optimization variables. By increasing the speed at which radiotherapy treatment plan optimization problems are solved, the disclosed techniques may enable real-time treatment planning to be performed and reduce wait time for patients and clinicians. Estimating optimization variables refers to generating an estimated value of one or more decision variables of a given optimization problem.

Specifically, the disclosed techniques receive a radiotherapy treatment plan optimization problem and process the radiotherapy treatment plan optimization problem with a machine learning model to estimate one or more optimization variables of the radiotherapy treatment plan optimization problem. The machine learning model is trained to establish a relationship between the one or more optimization variables and parameters of a plurality of training radiotherapy treatment plan optimization problems. A solution to the radiotherapy treatment plan optimization problem is generated based on the estimated one or more optimization variables of the radiotherapy treatment plan optimization problem. Radiotherapy treatment device parameters, e.g. control points, of a given device can then be determined and generated by the solved radiotherapy treatment plan optimization problem.

FIG. 1 illustrates an exemplary radiotherapy system 100 adapted to perform radiotherapy plan processing operations using one or more of the approaches discussed herein. These radiotherapy plan processing operations are performed to enable the radiotherapy system 100 to provide radiation therapy to a patient based on specific aspects of captured medical imaging data and therapy dose calculations or radiotherapy machine configuration parameters. Specifically, the following processing operations may be implemented as part of the treatment processing logic 120. It will be understood, however, that many variations and use cases of the following trained models and treatment processing logic 120 may be provided, including in data verification, visualization, and other medical evaluative and diagnostic settings.

The radiotherapy system 100 includes a radiotherapy processing computing system 110 which hosts treatment processing logic 120. The radiotherapy processing computing system 110 may be connected to a network (not shown), and such network may be connected to the Internet. For instance, a network can connect the radiotherapy processing computing system 110 with one or more private and/or public medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device), and a treatment data source 160.

As an example, the radiotherapy processing computing system 110 can be configured to receive a treatment goal of a subject (e.g., from one or more MR images) and generate a radiotherapy treatment plan by executing instructions or data from the treatment processing logic 120, as part of operations to generate treatment plans to be used by the treatment device 180 and/or for output on device 146. In an embodiment, the treatment processing logic 120 solves an optimization problem to generate the radiotherapy treatment plan. The treatment processing logic 120 solves the radiotherapy optimization problem using a trained ML model that has been trained to establish a relationship between the one or more optimization variables and parameters of a plurality of training radiotherapy treatment plan optimization problems. In an example, the treatment processing logic 120 classifies the optimization problem that is received into a particular type and then identifies a given ML model that has been trained to solve the particular type of optimization problem. The given ML model is applied to the received optimization problem to estimate optimization variables of the received optimization problem. Then, the optimization problem is solved using a conventional optimization problem solver (e.g., simplex method, an interior point method, a Newton method, a quasi-Newton method, a Gauss-Newton method, a Levenberg-Marquardt method, a linear least-squares method, a gradient descent method, a projected gradient method, a conjugate gradient method, an augmented Lagrangian method, a Nelder-Mead method, a branch and bound method, a cutting plane method, simulated annealing, and/or sequential quadratic programming) based on the estimated optimization variables.

A generic radiotherapy treatment plan optimization problem can be defined as Equation 1:

$$\underset{x \in X}{\text{minimize}} \; f(x) \quad (1)$$

subject to $x \in \Omega$ where $f: X \to \mathbb{R}$ is the objective function, $x \in X$ is the decision variables and $\Omega \subseteq X$ is the set of feasible variables. In general, the function $f$ can be nonlinear and the set $\Omega$ non-convex. The optimization problems are typically solved using some form of iterative scheme. For example, in case $f$ is smooth and convex, and $\Omega$ is convex, then the projected gradient scheme could be used to solve eq. (1) and reads as follows:

$$x_{n+1} = \text{proj}_\Omega(x_n - \eta \nabla f(x_n))$$

where $\text{proj}_\Omega: X \to X$ is the projection onto $\Omega$, $\eta \in \mathbb{R}$ is a stepsize and $\nabla f: X \to X$ the gradient. While these algorithms are typically provably convergent (e.g., given enough time (and correct parameter choices), the algorithm will converge to a minimizer), they are not always very fast and efficient. In fact, several algorithms may require hundreds if not thousands of iterations in order to achieve approximate convergence. Since each step may be computationally expensive, this may imply runtimes of minutes or even hours. According to the disclosed techniques, a trained ML model is used to expedite solving such optimization problems by estimating one or more optimization variables (e.g., x) of such problems and then applying the conventional methods to solve the optimization problems. In certain approaches, the ML model provides a solution to the optimization problems that is within a deviation threshold of a desired or expected solution. In such cases, conventional methods may not be needed as the solution to the optimization problem is estimated by the ML model.

Particularly, the disclosed embodiments enhance the speed and efficiency of solving the optimization problem using deep learning-based optimization. Namely, an optimization scheme is selected that is fine-tuned to the type of problems at hand. The deep learning optimization approach adds more parameters, in the form of a deep neural network, to the optimization problem and then picks the parameters that solve the optimization problem as well as possible (e.g., to a specified threshold deviation from the optimal solution).

The radiotherapy processing computing system 110 may include processing circuitry 112, memory 114, a storage device 116, and other hardware and software-operable features such as a user interface 142, a communication interface (not shown), and the like. The storage device 116 may store transitory or non-transitory computer-executable instructions, such as an operating system, radiation therapy treatment plans, training data, software programs (e.g., image processing software, image or anatomical visualization software, artificial intelligence (AI) or ML implementations and algorithms such as provided by deep learning models, ML models, and neural networks (NNs), etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application-specific integrated circuit (ASIC), a field programmable gate array (FPGA), a digital signal processor (DSP), a System on a Chip (SoC), or the like.

As would be appreciated by those skilled in the art, in some examples, the processing circuitry 112 may be a special-purpose processor rather than a general-purpose processor. The processing circuitry 112 may include one or more known processing devices, such as a microprocessor from the Pentium™, Core™ Xeon™, or Itanium® family manufactured by Intel™, the Turion™, Athlon™ Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry-based) or software-based processor (for example, a multi-core design or a plurality of processors each having a multi-core design). The processing circuitry 112 can execute sequences of transitory or non-transitory computer program instructions, stored in memory 114, and accessed from the storage device 116, to perform various operations, processes, and methods that will be explained in greater detail below. It should be understood that any component in system 100 may be implemented separately and operate as an independent device and may be coupled to any other component in system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, one or more ML model(s) or technique(s) parameters, data, or transitory or non-transitory computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting transitory or non-transitory machine-readable media.

The memory 114 and the storage device 116 may constitute a non-transitory computer-readable medium. For example, the memory 114 and the storage device 116 may store or load transitory or non-transitory instructions for one or more software applications on the computer-readable medium. Software applications stored or loaded with the memory 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory 114 and the storage device 116 may store or load an entire software application, part of a software application, or code or data that is associated with a software application, which is executable by the processing circuitry 112. In a further example, the memory 114 and the storage device 116 may store, load, and manipulate one or more radiation therapy treatment plans, imaging data, segmentation data, treatment visualizations, histograms or measurements, one or more AI model data (e.g., weights and parameters of the ML model(s) of the disclosed embodiments), training data, labels and mapping data, and the like. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, the network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., MR images) for hosting on the storage device 116 and the memory 114. In yet another example, the software programs may substitute functions of the patient images such as signed distance functions or processed versions of the images that emphasize some aspect of the image information.

In an example, the radiotherapy processing computing system 110 may obtain or communicate image data 152 from or to image data source 150. In further examples, the treatment data source 160 receives or updates the planning data as a result of a treatment plan generated by the treatment processing logic 120. The image data source 150 may also provide or host the imaging data for use in the treatment processing logic 120.

In an example, computing system 110 may communicate with treatment data source(s) 160 and input device 148 to generate pairs of one or more training optimization variables and training parameters of a plurality of training radiotherapy treatment plan optimization problems; pairs of one or more training optimization variables and training parameters of a plurality of training radiotherapy treatment plan optimization problems and solutions to the plurality of training radiotherapy treatment optimization problems; and pairs of one or more training optimization variables and training parameters of a plurality of training radiotherapy treatment plan optimization problems of a given type.

The processing circuitry 112 may be communicatively coupled to the memory 114 and the storage device 116, and the processing circuitry 112 may be configured to execute computer-executable instructions stored thereon from either the memory 114 or the storage device 116. The processing circuitry 112 may execute instructions to cause medical images from the image data 152 to be received or obtained in memory 114 and processed using the treatment processing logic 120 to generate a treatment plan. Particularly, treatment processing logic 120 receives an optimization problem that is derived based on the medical images that are received. The treatment processing logic implements a trained ML model that is applied to the optimization problem to estimate one or more optimization variables of the optimization problem. Once the optimization variables are estimated, the received optimization problem is solved using the estimated optimization variables to generate a treatment plan.

In addition, the processing circuitry 112 may utilize software programs to generate intermediate data such as updated parameters to be used, for example, by a NN model, machine learning model, treatment processing logic 120 or other aspects involved with generation of a treatment plan as discussed herein. Further, such software programs may utilize the treatment processing logic 120 to produce new or updated treatment plan parameters for deployment to the treatment data source 160 and/or presentation on output device 146, using the techniques further discussed herein. The processing circuitry 112 may subsequently then transmit the new or updated treatment plan parameters via a communication interface and the network to the treatment device 180, where the radiation therapy plan will be used to treat a patient with radiation via the treatment device 180, consistent with results of the trained ML model implemented by the treatment processing logic 120 (e.g., according to the processes discussed below in connection with FIG. 3).

In the examples herein, the processing circuitry 112 may execute software programs that invoke the treatment processing logic 120 to implement functions of ML, deep learning, NNs, and other aspects of artificial intelligence for treatment plan generation from an input radiotherapy medical information (e.g., CT image, MR image, and/or sCT image and/or dose information). For instance, the processing circuitry 112 may execute software programs that train, analyze, predict, evaluate, and generate a treatment plan parameter from received radiotherapy medical information as discussed herein.

In an example, the image data 152 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer-generated synthetic images (e.g., pseudo-CT images) and the like. Further, the image data 152 may also include or be associated with medical image processing data (for example, training images, ground truth images, contoured images, and dose images). In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., a MRI device combined with a linear accelerator, also referred to as an "MRI-Linac"). Such an MRI-Linac can be used, for example, to determine a location of a target organ or a target tumor in the patient so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, including control points of a radiotherapy treatment device, such as couch position, beam intensity, beam angles, dose-histogram-volume information, the number of radiation beams to be used during therapy, the dose per beam, and the like.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information (e.g., control points) may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.), treatment plans, a target, localizing a target and/or tracking a target, or any related information to the user. The input device 148 connected to the user interface 142 may be a keyboard, a keypad, a touch screen or any type of device that a user may use to the radiotherapy system 100. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D CBCT or CT or MRI volume. Such 2D slices can be acquired by the image acquisition device 170 in "near real time" while a patient is undergoing radiation therapy treatment (for example, when using the treatment device 180 (with "near real time" meaning acquiring the data in at least milliseconds or less)).

The treatment processing logic 120 in the radiotherapy processing computing system 110 implements a ML model, which involves the use of a trained (learned) ML model. This ML model may be provided by a NN trained as part of a NN model. One or more teacher ML models may be provided by a different entity or at an off-site facility relative to treatment processing logic 120 and is accessible by issuing one or more queries to the off-site facility.

Supervised machine learning CML) algorithms or ML models or techniques can be summarized as function approximation. Training data consisting of input-output pairs of some type (e.g., one or more training optimization variables and training parameters of a plurality of training radiotherapy treatment plan optimization problems) are acquired from, e.g., expert clinicians or prior optimization plan solvers and a function is "trained" to approximate this mapping. Some methods involve NNs. In these, a set of parametrized functions $A_\theta$ are selected, where $\theta$ is a set of parameters (e.g., convolution kernels and biases) that are selected by minimizing the average error over the training data. If the input-output pairs are denoted by $(x_m, y_m)$, the function can be formalized by solving a minimization problem such as Equation 2:

$$\min_\theta \sum_{m=1}^{M} \|A_\theta(x_m) - y_m\|^2 \qquad (2)$$

Once the network has been trained (e.g., $\theta$ has been selected), the function $A_\theta$ can be applied to any new input. For example, in the above setting of radiotherapy treatment plan optimization problem variables, a never-before-seen radiotherapy treatment plan optimization problem can be fed into $A_\theta$, and one or more radiotherapy treatment plan optimization problem variables are estimated that match what an optimization problem solver would find.

Simple NNs consist of an input layer, a middle or hidden layer, and an output layer, each containing computational units or nodes. The hidden layer(s) nodes have input from all the input layer nodes and are connected to all nodes in the output layer. Such a network is termed "fully connected." Each node communicates a signal to the output node depending on a nonlinear function of the sum of its inputs. For a classifier, the number of input layer nodes typically equals the number of features for each of a set of objects being sorted into classes, and the number of output layer nodes is equal to the number of classes. A network is trained by presenting it with the features of objects of known classes and adjusting the node weights to reduce the training error by an algorithm called backpropagation. Thus, the trained network can classify novel objects whose class is unknown.

Neural networks have the capacity to discover relationships between the data and classes or regression values, and under certain conditions, can emulate any function $y=f(x)$ including non-linear functions. In ML, an assumption is that the training and test data are both generated by the same data-generating process, $P_{data}$, in which each $\{x_i, y_i\}$ sample is identically and independently distributed (i.i.d.). In ML, the goals are to minimize the training error and to make the difference between the training and test errors as small as possible. Underfitting occurs if the training error is too large; overfitting occurs when the train-test error gap is too large. Both types of performance deficiency are related to model capacity: large capacity may fit the training data very well but lead to overfitting, while small capacity may lead to underfitting.

Figure 2A:
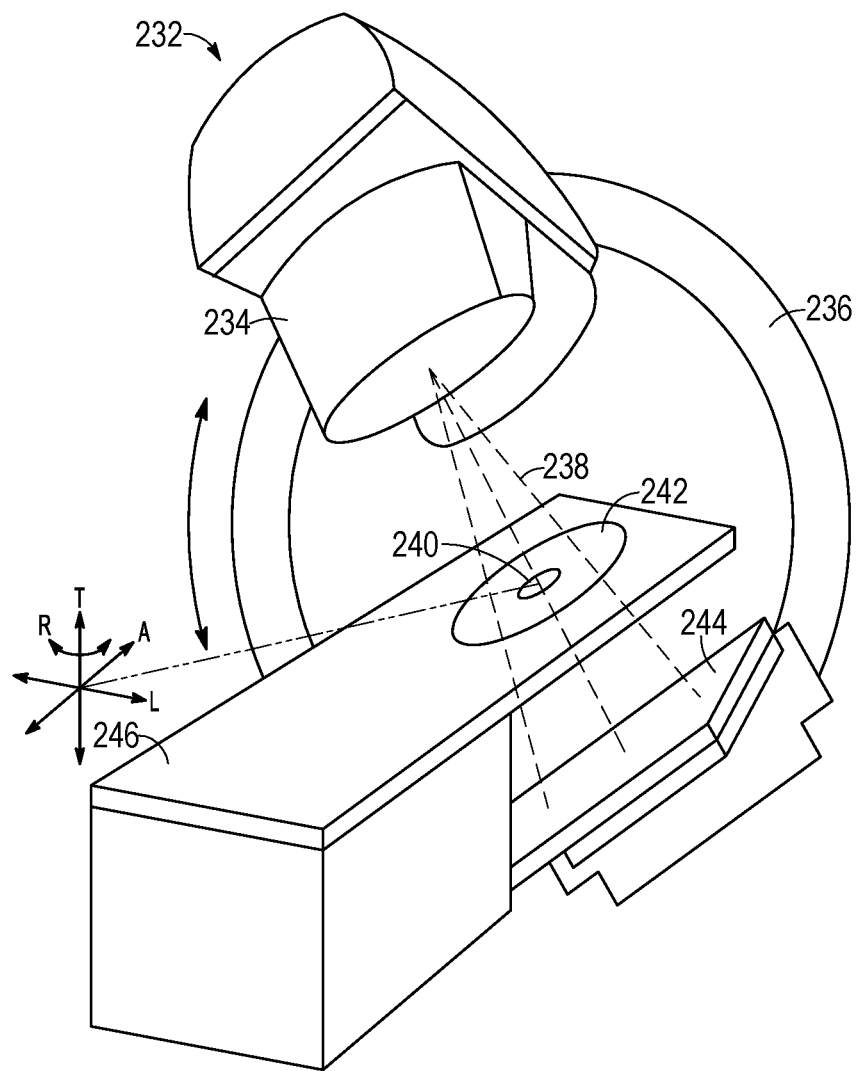
FIG. 2A illustrates an exemplary image-guided radiotherapy device, according to some examples of the disclosure.

FIG. 2A illustrates an exemplary image-guided radiation therapy device 232 that includes a radiation source, such as an X-ray source or a linear accelerator, a couch 246, an imaging detector 244, and a radiation therapy output 234. The radiation therapy device 232 may be configured to emit a radiation therapy beam 238 to provide therapy to a patient. The radiation therapy output 234 can include one or more attenuators or collimators, such as a MLC.

As an example, a patient can be positioned in a region 242, supported by the treatment couch 246, to receive a radiation therapy dose according to a radiation therapy treatment plan. The radiation therapy output 234 can be mounted or attached to a gantry 236 or other mechanical support. One or more chassis motors (not shown) may rotate the gantry 236 and the radiation therapy output 234 around the couch 246 when the couch 246 is inserted into the treatment area. In an example, gantry 236 may be continuously rotatable around couch 246 when the couch 246 is inserted into the treatment area. In another example, gantry 236 may rotate to a predetermined position when the couch 246 is inserted into the treatment area. For example, the gantry 236 can be configured to rotate the therapy output 234 around an axis ("A"). Both the couch 246 and the radiation therapy output 234 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 246's movements or rotations in order to properly position the patient in or out of the radiation therapy beam 238, according to a radiation therapy treatment plan. Both the couch 246 and the gantry 236 are independently moveable from one another in multiple degrees of freedom, which allows the patient to be positioned such that the radiation therapy beam 238 can precisely target the tumor.

The coordinate system (including axes A, T, and L) can have an origin located at an isocenter 240. The isocenter 240 can be defined as a location where the central axis of the radiation therapy beam 238 intersects the origin of a coordinate axis, such as to deliver a prescribed radiation dose to a location on or within a patient. Alternatively, the isocenter 240 can be defined as a location where the central axis of the radiation therapy beam 238 intersects the patient for various rotational positions of the radiation therapy output 234 as positioned by the gantry 236 around the axis A.

Gantry 236 may also have an attached imaging detector 244. The imaging detector 244 is preferably located opposite to the radiation source (output 234) and, in an example, the imaging detector 244 can be located within a field of the therapy beam 238. The imaging detector 244 can be mounted on the gantry 236, preferably opposite the radiation therapy output 234, so as to maintain alignment with the radiation therapy beam 238. The imaging detector 244 rotates about the rotational axis as the gantry 236 rotates. In an example, the imaging detector 244 can be a flat panel detector (e.g., a direct detector or a scintillator detector). In this manner, the imaging detector 244 can be used to monitor the radiation therapy beam 238, or the imaging detector 244 can be used for imaging the patient's anatomy, such as portal imaging. The control circuitry of radiation therapy device 232 may be integrated within the radiotherapy system 100 or remote from it.

In an illustrative example, one or more of the couch 246, the therapy output 234, or the gantry 236 can be automatically positioned, and the therapy output 234 can establish the therapy beam 238 according to a specified dose for a particular therapy delivery instance. A sequence of therapy deliveries can be specified according to a radiation therapy treatment plan, such as using one or more different orientations or locations of the gantry 236, couch 246, or therapy output 234. The therapy deliveries can occur sequentially but can intersect in a desired therapy locus on or within the patient, such as at the isocenter 240. A prescribed cumulative dose of radiation therapy can thereby be delivered to the therapy locus while damage to tissue nearby the therapy locus can be reduced or avoided.

Thus, FIG. 2A specifically illustrates an example of a radiation therapy device 232 operable to provide radiotherapy treatment to a patient consistent with or according to a radiotherapy treatment plan, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, and the like, as would be recognized by one of ordinary skill in the art.

Figure 2B:
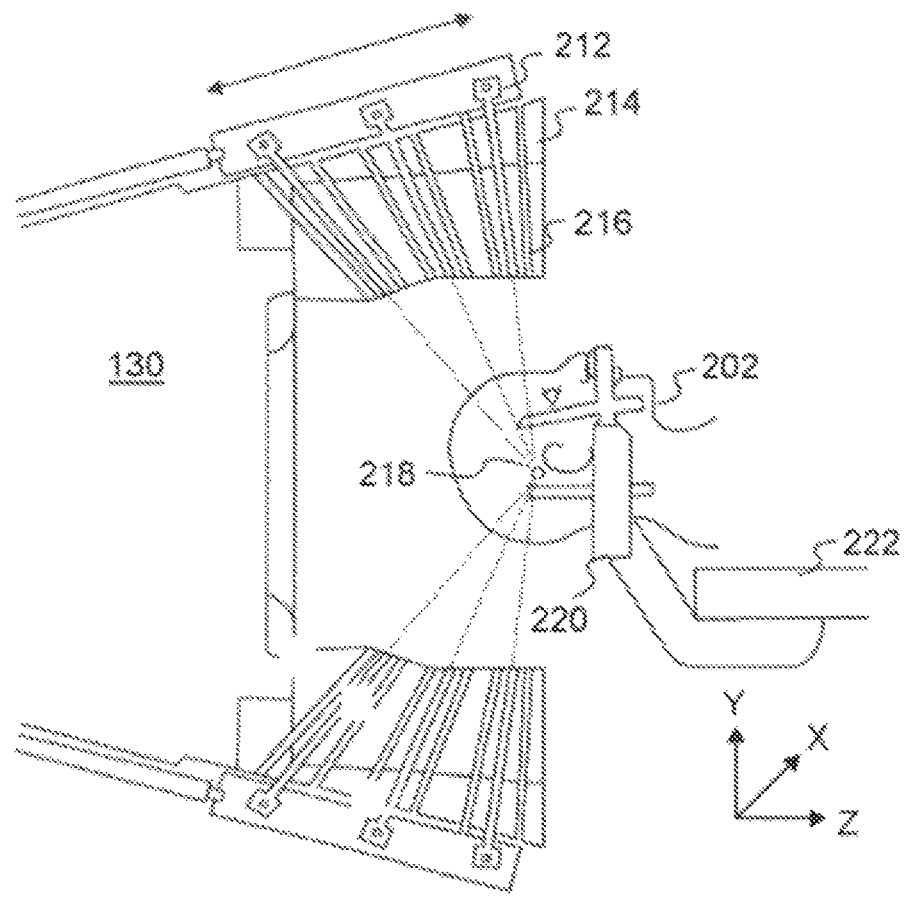
FIG. 2B illustrates a radiation therapy device, a Gamma Knife, according to some examples of the disclosure.

FIG. 2B illustrates a radiotherapy device 130, a Gamma Knife in which the present disclosure can be used. A patient 202 may wear a coordinate frame 220 to keep stable the patient's body part (e.g. the head) undergoing surgery or radiotherapy. Coordinate frame 220 and a patient positioning system 222 may establish a spatial coordinate system, which may be used while imaging a patient or during radiation surgery. Radiotherapy device 130 may include a protective housing 214 to enclose a plurality of radiation sources 212 for generation of radiation beams (e.g. beamlets) through beam channels 216. The plurality of beams may be configured to focus on an isocenter 218 from different locations. While each individual radiation beam may have relatively low intensity, isocenter 218 may receive a relatively high level of radiation when multiple doses from different radiation beams accumulate at isocenter 218. In certain embodiments, isocenter 218 may correspond to a target under surgery or treatment, such as a tumor.

As an example of an embodiment, an output element may include a dose to be applied to a voxel of a particular OAR. Further, a feature element may be used to determine the output element. The feature element may include a distance between the voxel in the OAR and the closest boundary voxel in a target tumor. Therefore, the feature element may include a signed distance x indicating the distance between a voxel in an OAR and the closest boundary voxel in a target for the radiation therapy. The output element may include a dose D in the voxel of the OAR from which x is measured. In some other embodiments, each training sample may correspond to a particular voxel in the target or OAR, such that multiple training samples within the training data correspond to the whole volume of the target or OAR and other anatomical portions subject to the radiotherapy treatment.

Figure 3:
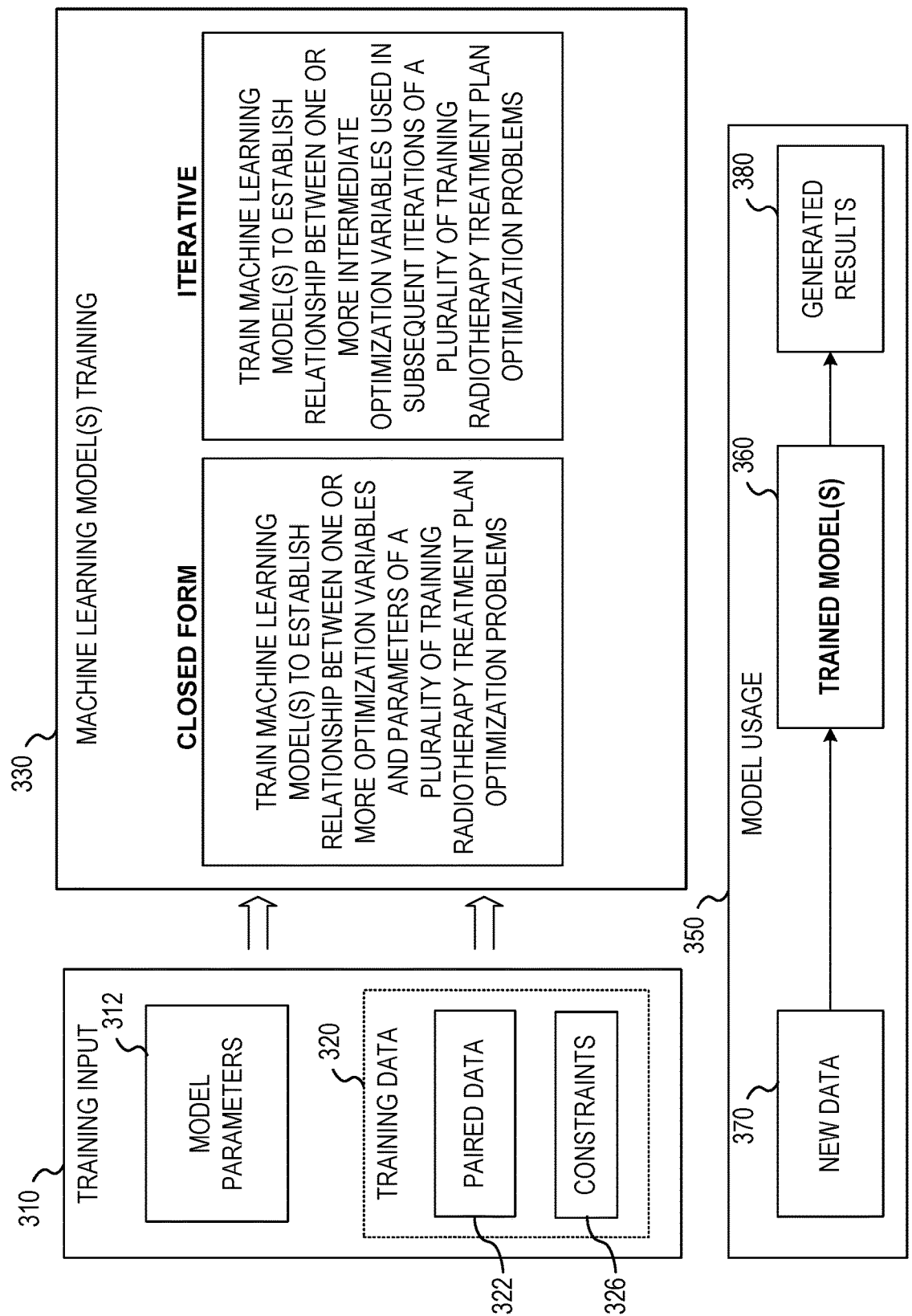
FIG. 3 illustrates an exemplary data flow for training and use of a machine learning technique to solve a radiotherapy treatment plan optimization problem, according to some examples of the disclosure.

FIG. 3 illustrates an exemplary data flow for training and use of machine learning model(s) to solve a radiotherapy treatment plan optimization problem, according to some examples of the disclosure. The data flow includes training input 310, ML model(s) (technique(s)) training 330, and model(s) usage 350.

Training input 310 includes model parameters 312 and training data 320 which may include paired training data sets 322 (e.g., input-output training pairs) and constraints 326. Model parameters 312 stores or provides the parameters or coefficients of corresponding ones of machine learning models $A_9$. During training, these parameters 312 are adapted based on the input-output training pairs of the training data sets 322. After the parameters 312 are adapted (after training), the parameters are used by trained treatment models 360 to implement the respective one of the trained machine learning models—on a new set of data 370.

Training data 320 includes constraints 326 which may define the physical constraints of a given radiotherapy device. The paired training data sets 322 may include sets of input-output pairs, such as a pairs of one or more training optimization variables and training parameters of a plurality of training radiotherapy treatment plan optimization problems; pairs of one or more training optimization variables and training parameters of a plurality of training radiotherapy treatment plan optimization problems and solutions to the plurality of training radiotherapy treatment optimization problems; and pairs of one or more training optimization variables and training parameters of a plurality of training radiotherapy treatment plan optimization problems of a given type. Some components of training input 310 may be stored separately at a different off-site facility or facilities than other components. In an embodiment, each machine learning model $\hat{A}_\theta$ may be trained on a particular type of optimization problem that has been classified. Particularly, the classification problems in the training data 230 can be grouped according to type and the training data for each particular type is used to train a corresponding machine learning model. In this way, when a new optimization problem is encountered or received, the new optimization problem is classified to determine its type and the corresponding ML model trained on that particular type can be accessed to estimate optimization variables of the new optimization problem.

Machine learning model(s) training 330 trains one or more machine learning techniques $\hat{A}_\theta$ based on the sets of input-output pairs of paired training data sets 322. For example, the model training 330 may train the ML model parameters 312 by minimizing a first loss function based on one or more training optimization variables and the corresponding training parameters of a corresponding one of the plurality of training radiotherapy treatment plan optimization problems.

The result of minimizing the loss function for multiple sets of training data trains, adapts, or optimizes the model parameters 312 of the corresponding ML models. In this way, the ML model is trained to establish a relationship between one or more optimization variables and parameters of a plurality of training radiotherapy treatment plan optimization problems.

In some embodiments, the ML model is trained to estimate one or more optimization variables of a radiotherapy treatment plan optimization problem in closed form. In such cases, the one or more optimization variables can be used to directly solve the given radiotherapy treatment plan optimization problem. Particularly, the closed form solution defines a neural network $\Lambda_\theta$ which maps $f$ (the optimization problem function) to an approximation of the optimal solution x*.

The ML model trained to be applied and provide a closed form solution is trained in one implementation according to supervised learning techniques. Supervised learning techniques assume that $x_f^* = \arg\min_x f(x)$ is known from previously solving the optimization problem. In such cases, a distance function d is defined such that a distance to the solution is represented by $d(\Lambda_\theta(f), x_f^*)$. In such cases, to train the ML model $\Lambda_\theta$, a plurality of training optimization problems that have previously been solved for other patients (and/or that include synthetically generated problems) are retrieved together with their corresponding training parameters (e.g., optimization variables and solutions). The ML model is applied to a first batch of training optimization problems to estimate a given set of parameters (e.g., optimization variables and/or solutions). The batch of the training optimization problems can be used to train the ML model with the same parameters of the ML model and may range from one training optimization problem to all of the training problems. The output or result of the ML model is compared with the corresponding training parameters of the first batch of training optimization problems and a deviation is computed between the output or result and the corresponding training parameters of the first batch of training optimization problems using a loss function $\ell(\theta, f)$ or $L(\theta)$ discussed below. Based on this deviation, updated parameters for the ML model are computed. The ML model is then applied with the updated parameters to a second batch of training optimization problems to again estimate a given set of parameters for comparison with the parameters previously determined for the second batch of training optimization problem. Parameters of the ML model are again updated and iterations of this training process continue for a specified number of iterations or epochs or until a given convergence criteria has been met.

As referred to in this disclosure, "objective function" $f$ can include any one or combination of: the true objective function of the optimization problem; the extended objective function, which agrees with the true objective function on the feasible set but is infinite outside the feasible set; a merit function, which is a "softer" version of the extended objective function in that the merit function agrees with the true objective function on the feasible set and grows larger (but still finite) the further you are from the feasible set; and/or a relaxation of the objective function. For example, a linear programming relaxation of an integer programming problem removes the integrality constraint and so allows non-integer rational solutions. A Lagrangian relaxation of a complicated problem in combinatorial optimization penalizes violations of some constraints, allowing an easier relaxed problem to be solved. Relaxation techniques complement or supplement branch and bound algorithms of combinatorial optimization; linear programming and Lagrangian relaxations are used to obtain bounds in branch-and-bound algorithms for integer programming.

The ML model trained to be applied and provide a closed form solution is trained in one implementation according to unsupervised learning techniques, wherein the true solution is not used (regardless of whether it's known or not). The closed form function value is defined by $f(\Lambda_\theta(f))$. In such cases, to train the ML model $\Lambda_\theta$, a plurality of training optimization problems for other patients (and/or that include synthetically generated problems) are retrieved. The ML model is applied to a first batch of the training optimization problems to estimate a given set of parameters (e.g., optimization variables, active set of constraints, such as which constraints that are active at the solution, and/or solutions). The batch of the training optimization problems can be used to train the ML model with the same parameters of the ML model and may range from one training optimization problem to all of the training problems. The output or result of the ML model is evaluated using a loss function $\ell(\theta, f)$ or $L(\theta)$ discussed below to obtain feedback on the loss/utility of the current iteration. Based on this loss function, updated parameters for the ML model are computed. The ML model is then applied with the updated parameters to a second batch of training optimization problems to again estimate a given set of parameters. Parameters of the ML model are again updated and iterations of this training process continue for a specified number of iterations or epochs or until a given convergence criteria has been met.

In some embodiments, the ML model is trained to estimate one or more optimization variables of a radiotherapy treatment plan optimization problem in an iterative approach. In such cases, the ML model estimates one or more intermediate optimization variables for one or more iterations of solving the optimization problem. In some implementations, intermediate optimization variables from one iteration of processing the optimization problem with the ML model are processed recursively by another iteration of processing the optimization problem with the ML model. After a certain number of iterations or when a stopping criterion is met, the solution to optimization problem can be output and used to generate a radiotherapy treatment plan. Alternatively, after the stopping criterion is met, the optimization problem with the last estimated intermediate optimization variables can be further solved using other optimization problem solving techniques. The iterative solution defines an initial guess $x_0$ and a neural network $\Lambda_\theta$ which maps each iteration to the next $x_{n+1} = \Gamma_\theta(f, x_n, \ldots, x_0)$, where the goal is for $x_n \to x^*$.

The ML model trained to be applied and provide an iterative form solution is trained in one implementation according to supervised training techniques. In such cases, a distance function d is defined such that a distance to the solution after n iterations is $d(x_{nN}, x_f^*)$. In some cases, the ML model is trained to estimate optimization variables such that the error after a given number N of iterations is as small as possible, i.e. $\ell(\theta, f) = d(x_N, x_f^*)$. In other cases, the ML model is trained to estimate optimization variables such that the number of iterations needed to reach a specified error is as small as possible, i.e. $\ell(\theta, f) = \min\{n \in \mathbb{N} : d(x_n, x^*) < \epsilon\}$. In yet other cases, the ML model is trained to estimate optimization variables such that the weighted average function value over a given set of iterations is as small as possible, i.e. $\ell(\theta, f) = \Sigma_n w_n d(x_n, x^*)$. In some cases, to train the iterative ML model $\Lambda_\theta$, a plurality of training optimization problems previously solved iteratively (for some specified fixed number of iterations or that have been solved to completion) for other patients (and/or that include synthetically generated problems) are retrieved together with their corresponding iterative training parameters (e.g., optimization variables and solutions for each iteration or the final set of parameters corresponding to the solution). The ML model is applied to a first batch of the training optimization problems to estimate a given intermediate set of parameters (e.g., optimization variables and/or solutions). The batch of the training optimization problems can be used to train the ML model with the same parameters of the ML model and may range from one training optimization problem to all of the training problems. The output or result of the ML model is compared with the corresponding training parameters of the first batch of training optimization problems and a deviation is computed between the output or result and the corresponding training parameters of the first batch of training optimization problems using a loss function $\ell(\theta, f)$ or $L(\theta)$ discussed below. Based on this deviation, updated parameters for the ML model are computed. The ML model is then applied with the updated parameters to a second batch of training optimization problems to again estimate a given set of parameters for comparison with the parameters previously determined for the second batch of training optimization problems. Parameters of the ML model are again updated, and iterations of this training process continue for a specified number of epochs or until all of the training optimization problems are processed.

The ML model trained to be applied and provide an iterative solution is trained in one implementation according to unsupervised learning techniques, wherein the true solution is not used (regardless of whether it's known or not). In such cases, to train the ML model $\Lambda_\theta$, a plurality of training optimization problems for other patients (and/or that include synthetically generated problems) are retrieved. The ML model is applied to a first batch of the training optimization problems to estimate a given set of parameters (e.g., optimization variables, active set of constraints, such as which constraints that are active at the solution, and/or solutions). The ML model is recursively and iteratively applied to the first batch of the training optimization problems such that intermediate optimization variables from one iteration of processing the optimization problem with the ML model are processed recursively by another iteration of processing the optimization problem with the ML model until a certain number of iterations or when a stopping criterion is met. The output or result of the ML model after the stopping criterion is met is evaluated using a loss function $\ell(\theta, f)$ or $L(\theta)$ discussed below to obtain feedback on the loss/utility of the current iteration. Namely, the function value after a fixed number of iterations, for some $N \in \mathbb{N}$, $\ell(\theta, f) = f(x_N)$. The weighted average function value is computed $\ell(\theta, f) = \Sigma_n w_n f(x_n)$ where $w_n$ are weights. Based on this loss function, updated parameters for the ML model are computed. The ML model is then applied iteratively and recursively with the updated parameters to a second batch of training optimization problems to again estimate a given set of parameters iteratively. Parameters of the ML model are again updated and iterations of this training process continue for a specified number of iterations or epochs or until a given convergence criteria has been met.

Specifically, the ML model is trained in a supervised or unsupervised manner based on the loss function such that the intermediate set of parameters estimated by the ML model for a given optimization problem represent the solution to the given optimization problem after the specified fixed number of iterations or the solution to the given optimization problem after the problem has been completely solved. The ML model is trained until a stopping criteria is met (e.g., a maximum number of iterations has been reached, a decrease in objective value is achieved, a step length is met, etc.) or when a solution is within a specified threshold error of the final solution to the given optimization problem or is within a specified threshold error of the solution after the specified number of iterations. In this way, this trained ML model can be applied to a new optimization problem to estimate one or more optimization variables of the new optimization problem. In some cases, the new optimization problem can be iteratively and recursively solved using the estimated optimization variables by applying the ML model recursively for a number of iterations. In some instances, the number of iterations required to solve the new optimization problem recursively is less than the total number of iterations it would have taken to solve the optimization problem using the initial optimization variables using conventional techniques. In some cases, the new optimization problem with the estimated optimization variables that result from applying the ML model can be solved using other optimization solving techniques.

In some cases, the ML model that is trained depends on the classification of the optimization problems in the training set. For example, the closed form ML model, if the target function $f$ is parametrized by images (e.g., dose plans and tomographic images) can be a U-Net that could be used to predict the optimal decision variables. For an ML model used to provide an iterative solution, a learned projected gradient scheme can be used given by $x_{n+1} = \text{proj}_\Omega(x_n - \eta \nabla f(x_n) + \Lambda_{\theta_n}(f, x_n, \ldots, x_0))$, where $\Lambda_{\theta_n}: X \to X$ are deep neural networks and $\theta = (\theta_1, \ldots, \theta_N)$ are their parameters.

Loss functions are all defined for a specific optimization problem, but in practice the problem that needs to be solved is unknown. As such, an optimization solver cannot be specialized to solve only one specific optimization problem. Rather the solver needs to work on a family of related problems. The loss function should thus only depend on the parameter choice, $L(\theta)$. To do this, $f$ is assumed to be randomly drawn from some set of possible optimization problems endowed with a probability distribution.

After each of the machine learning models $\hat{A}_\theta$ (sometimes referred to as $\Lambda_\theta$) is trained, new data 370, including one or more patient input parameters (e.g., a radiotherapy treatment plan optimization problem), may be received. The trained machine learning technique $\hat{A}_\theta$ may be applied to the new data 370 to generate generated results 380 including one or more estimated optimization variables of the radiotherapy treatment plan optimization problem. The generated one or more estimated optimization variables of the radiotherapy treatment plan optimization problem are then used to solve the received optimization problem such as by using a simplex method, an interior point method, a Newton method, a quasi-Newton method, a Gauss-Newton method, a Levenberg-Marquardt method, a linear least-squares method, a gradient descent method, a projected gradient method, a conjugate gradient method, an augmented Lagrangian method, a Nelder-Mead method, a branch and bound method, a cutting plane method, simulated annealing, and/or sequential quadratic programming.

In some implementations, the new radiotherapy treatment plan optimization problem (that includes at least one of images of a patient or patient volume, a segmentation of the patient volume, a dose kernel, a dose volume histogram constraint, or a dose constraint) can be solved using the estimated optimization variables that are provided by the ML model. The solution to the optimization problem includes at least one of radiotherapy device parameters, fluence maps, shot positions, or beam-on times. In certain cases, to further simplify solving the new radiotherapy treatment plan optimization problem that is constrained (e.g., an optimization problem that is subject to certain constraints), the new radiotherapy treatment plan optimization problem can be first converted to an unconstrained optimization problem. This may be done before, during, or after the optimization variables are estimated by the ML model for the new radiotherapy treatment plan optimization problem. To represent the constrained radiotherapy treatment plan optimization problem as an unconstrained optimization problem, a merit function can be used. If the optimization problem is converted to an unconstrained optimization problem before estimating the optimization variables by the ML model, the unconstrained optimization problem can be processed by the ML model to estimate the optimization variables of the new optimization problem that are then used to solve the new optimization problem.

As an example, a generic radiotherapy treatment plan optimization problem can often be written as:

$$\underset{x}{\text{minimize}} \; f(x)$$
$$\text{subject to } c_i(x) = 0, \; i \in \varepsilon$$
$$c_i(x) \geq 0, \; i \in I$$

where $f$ is the objective function, $x$ are the decision variables and $\{c_i\}$ is a set of functions where $\varepsilon$ and $I$ are the sets of indices corresponding to equality and inequality constraints, respectively.

An example merit function for nonlinear programming problems includes the $\ell_1$ penalty function:

$$\phi(x; \mu) = f(x) + \mu \sum_{i \in \varepsilon} |c_i(x)| + \mu \sum_{i \in I} \max(0, -c_i(x)).$$

The positive scalar $\mu$ is a penalty parameter that determines the weight assigned to constraint satisfaction relative to minimization of the objective. The $\ell_1$ penalty function is an example of an exact merit function, which means that if $\mu$ is large enough, then any local solution of the optimization problem is a local minimizer of $\phi(x; \mu)$. As such, the disclosed techniques can perform a fixed but small number of iterations on the unconstrained problem:

$$\underset{x}{\text{minimize}}$$

$\phi(x; \mu)$ with a suitable algorithm for unconstrained optimization and use the result as the initial guess for an ordinary solver for constrained optimization. Specifically, a less complex unconstrained optimization problem solver can be used after applying the merit function to the radiotherapy treatment plan optimization problem to convert from a constrained to an unconstrained optimization problem. After a suitable number of iterations of the unconstrained optimization problem solver, the unconstrained optimization problem can be processed by a constrained optimization problem solver.

In some cases, after a suitable number of iterations of the unconstrained optimization problem solver, the ML model is applied to the unconstrained optimization problem to estimate one or more radiotherapy treatment plan optimization variables. The estimated one or more radiotherapy treatment plan optimization variables can then be applied to the radiotherapy treatment plan optimization problem, which can be solved by the constrained optimization problem solver.

The objective function of a radiotherapy treatment plan optimization problem can be decomposed into individual parts. For example, some parts include different objectives related to how well the tumor is targeted and other parts focus on sparing healthy tissue. Likewise, the set of feasible variables of the radiotherapy treatment plan optimization problem can be decomposed. For example, each beam-on time may have to be positive. This leads to optimization problems that can be defined as:

$$\text{minimize}_{x \in X} \sum_i f_i(x)$$

$$\text{subject to } x \in \bigcap_{j=1}^{J} \Omega_j$$

In these cases, iterative optimization algorithms can take this structure into account to speed up the optimization. For example, in randomized constraint projections the projection is only performed on a subset of all constraints in each iteration:

Pick $I_n \subseteq \{1, \ldots, J\}$ randomly $$x_{n+1} = \text{proj}_{\bigcap_{i \in I_n} \Omega_i}(x_n - \eta \nabla f(x_n))$$

Specifically, to further speed up solving the radiotherapy treatment plan optimization problem, a first set of constraints can be selected (e.g., randomly) and the radiotherapy treatment plan optimization problem is solved in a first iteration based on the first set of constraints that are selected. Subsequently, in one or more further iterations, a second set of constraints can be selected (e.g., randomly), and the radiotherapy treatment plan optimization problem is solved in the one or more further iterations based on the second set of constraints that are selected. In some cases, at each iteration, the ML model suitable for providing an iterative solution or intermediate set of optimization variables can be applied at each iteration as follows:

Pick $I_n \subseteq \{1, \ldots, J\}$ randomly $$x_{n+1} = \text{proj}_{\bigcap_{i \in I_n} \Omega_i}(x_n - \eta \nabla f(x_n) + \Lambda_{\theta_n}(f, x_n, \ldots, x_0)).$$

As an example, a first ML model can be trained to provide intermediate iterative optimization problem variables (e.g., a solution) for a given radiotherapy treatment plan optimization problem that considers a certain set of constraints (e.g., a certain number of constrains) after a first number of iterations (e.g., one iteration of solving the optimization problem). In such cases, in a first iteration, the ML model can be applied to a new radiotherapy treatment plan optimization problem for which a random set of constraints are selected (corresponding to the certain number of constraints). The ML model provides intermediate iterative optimization problem variables (e.g., an intermediate solution or updated values of the optimization problem decision variables) of the new radiotherapy treatment plan optimization problem. In a second iteration, a second set of constraints of the radiotherapy treatment plan optimization problem can be selected and the first ML model or a second ML model can be applied to the radiotherapy treatment plan optimization problem with the second set of constraints to provide updated intermediate iterative optimization problem variables of the new radiotherapy treatment plan optimization problem. In some cases, the second ML model can be trained to provide intermediate iterative optimization problem variables (e.g., an intermediate solution or updated values of the optimization problem decision variables) for a given radiotherapy treatment plan optimization problem that considers a certain set of constraints (e.g., a certain number of constrains) after a second number of iterations (e.g., two iterations of solving the optimization problem). The updated intermediate iterative optimization problem variables correspond to the radiotherapy treatment plan optimization problem variables that result after performing two iterations. This process can be repeated for any number of additional iterations n.

In some embodiments, processing the radiotherapy treatment plan optimization problem with the machine learning model to estimate the one or more optimization variables comprises: selecting a first subset of constraints of the radiotherapy treatment plan optimization problem; performing a first iteration of processing the radiotherapy treatment plan optimization problem with the machine learning model to generate a first estimate of the one or more optimization variables based on the selected first subset of the constraints; selecting a second subset of constraints of the radiotherapy treatment plan optimization problem; and performing a second iteration of processing the radiotherapy treatment plan optimization problem with the machine learning model to generate a second estimate of the one or more optimization variables based on the selected second subset of the constraints. In some cases, the first and second subsets of constraints are selected randomly.

Figure 4:
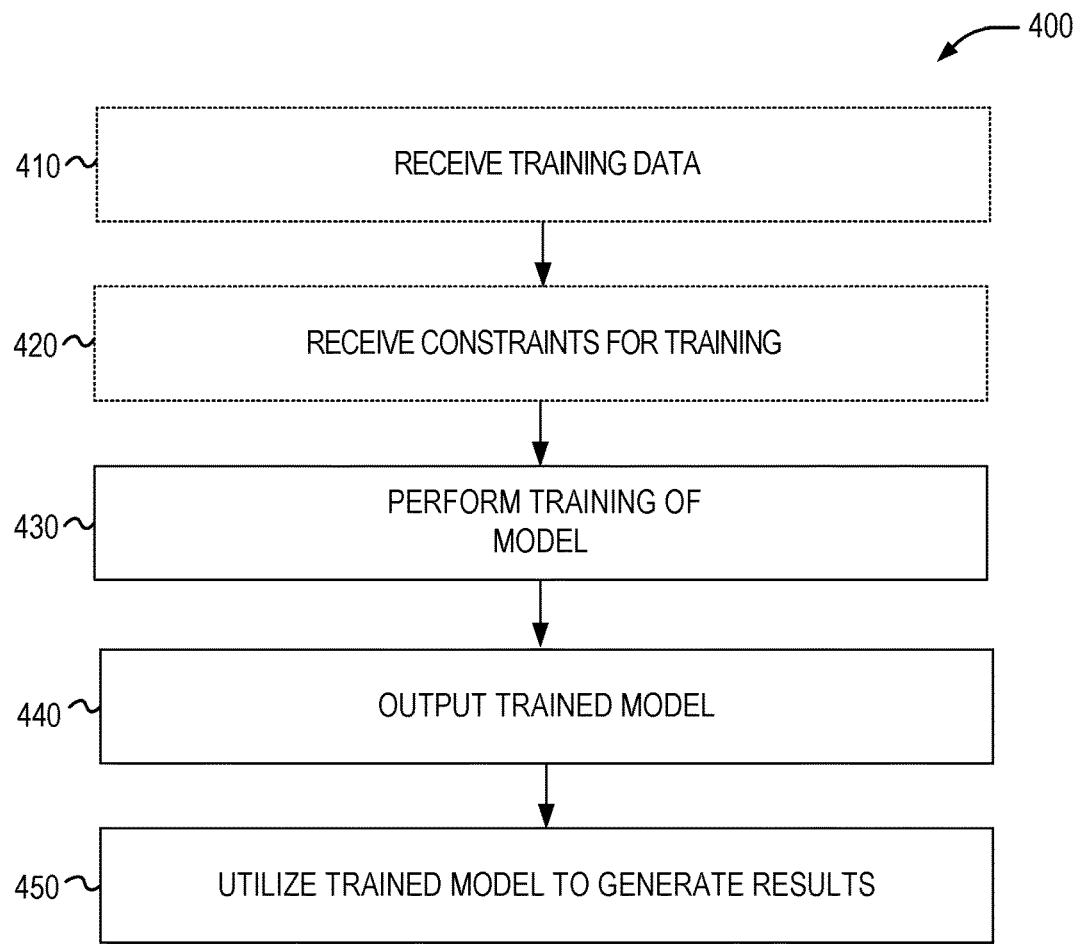
FIGS. 4-6 illustrate flowcharts of exemplary operations for training and using a machine learning technique to solve a radiotherapy treatment plan optimization problem, according to some examples of the disclosure.

FIG. 4 is a flowchart illustrating example operations of the treatment processing logic 120 in performing process 400, according to example embodiments. The process 400 may be embodied in computer-readable instructions for execution by one or more processors such that the operations of the process 400 may be performed in part or in whole by the functional components of the treatment processing logic 120; accordingly, the process 400 is described below by way of example with reference thereto. However, in other embodiments, at least some of the operations of the process 400 may be deployed on various other hardware configurations. The process 400 is therefore not intended to be limited to the treatment processing logic 120 and can be implemented in whole, or in part, by any other component. Some or all of the operations of process 400 can be in parallel, out of order, or entirely omitted.

At operation 410, treatment processing logic 120 receives training data. For example, treatment processing logic 120 receives pairs of one or more training optimization variables and training parameters of a plurality of training radiotherapy treatment plan optimization problems; pairs of one or more training optimization variables and training parameters of a plurality of training radiotherapy treatment plan optimization problems and solutions to the plurality of training radiotherapy treatment optimization problems; and pairs of one or more training optimization variables and training parameters of a plurality of training radiotherapy treatment plan optimization problems of a given type.

At operation 420, treatment processing logic 120 receives constraints for training.

At operation 430, treatment processing logic 120 performs training of the model. For example, treatment processing logic 120 may train the ML model parameters 312 (FIG. 3) by minimizing a first loss function based on one or more training optimization variables and the corresponding training parameters of a corresponding one of the plurality of training radiotherapy treatment plan optimization problems. In this way, the ML model is trained to establish a relationship between one or more optimization variables and parameters of a plurality of training radiotherapy treatment plan optimization problems. The training can be performed in a supervised or unsupervised manner and generates a closed form or iterative approach model.

At operation 440, treatment processing logic 120 outputs the trained model. For example, the trained model can be output and stored in a memory or parameters of the model can be presented on a display device to a clinician.

At operation 450, treatment processing logic 120 utilizes the trained model to generate results. For example, after each of the machine learning models $\hat{A}_\theta$ (sometimes referred to as $\Lambda_\theta$) is trained, new data 370, including one or more patient input parameters (e.g., a radiotherapy treatment plan optimization problem), may be received. The trained machine learning technique $\hat{A}_\theta$ may be applied to the new data 370 to generate generated results 380 including one or more estimated optimization variables of the radiotherapy treatment plan optimization problem. The new radiotherapy treatment plan optimization problem (that includes at least one of images of a patient or patient volume, a segmentation of the patient volume, a dose kernel, a dose volume histogram constraint, or a dose constraint) can be solved using the estimated optimization variables that are provided by the ML model.

Figure 5:
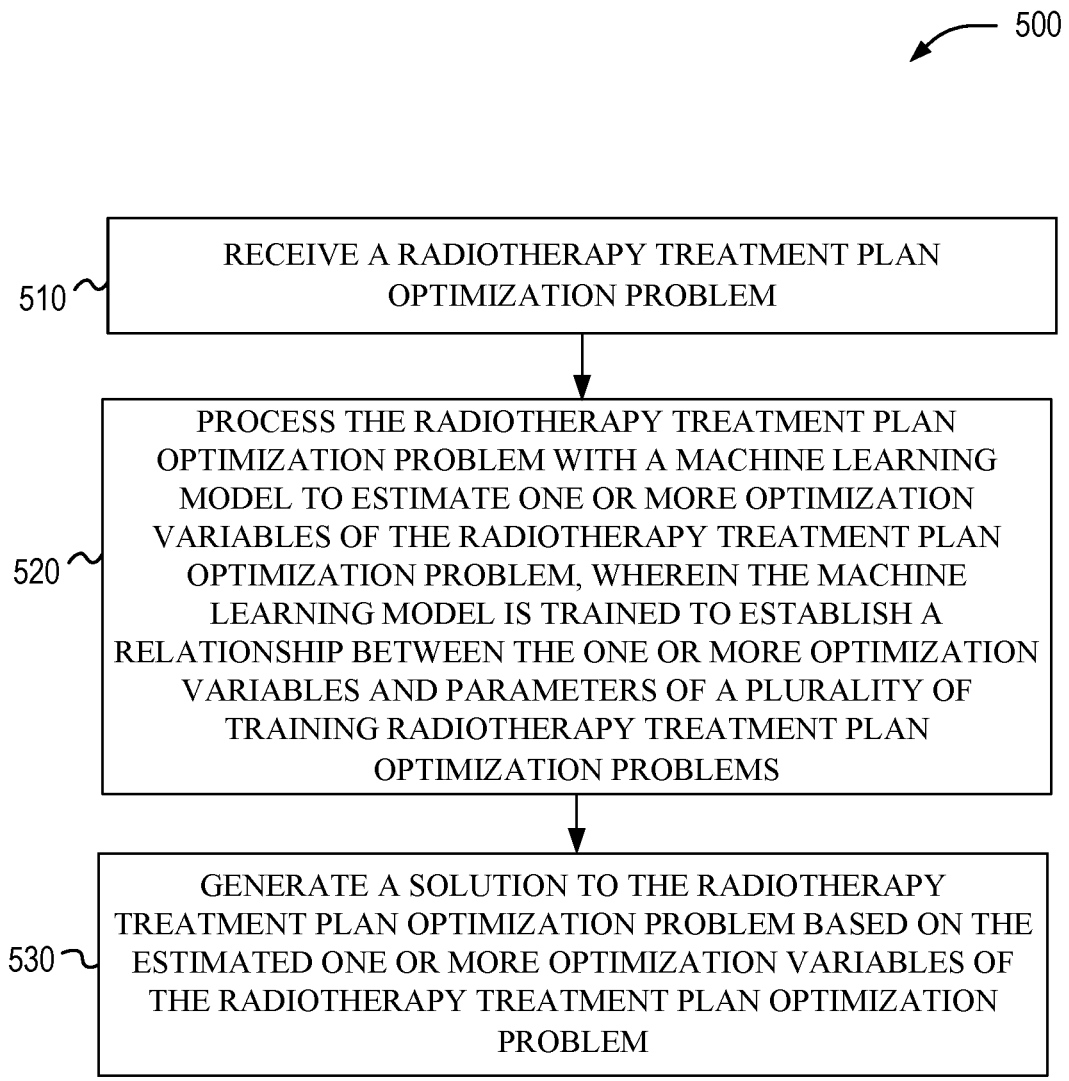

FIG. 5 is a flowchart illustrating example operations of the treatment processing logic 120 in performing process 500, according to example embodiments. The process 500 may be embodied in computer-readable instructions for execution by one or more processors such that the operations of the process 500 may be performed in part or in whole by the functional components of the treatment processing logic 120; accordingly, the process 500 is described below by way of example with reference thereto. However, in other embodiments, at least some of the operations of the process 500 may be deployed on various other hardware configurations. The process 500 is therefore not intended to be limited to the treatment processing logic 120 and can be implemented in whole, or in part, by any other component. Some or all of the operations of process 500 can be in parallel, out of order, or entirely omitted.

At operation 510, treatment processing logic 120 receives a radiotherapy treatment plan optimization problem.

At operation 520, treatment processing logic 120 processes the radiotherapy treatment plan optimization problem with a machine learning model to estimate one or more optimization variables of the radiotherapy treatment plan optimization problem, wherein the machine learning model is trained to establish a relationship between the one or more optimization variables and parameters of a plurality of training radiotherapy treatment plan optimization problems.

At operation 530, treatment processing logic 120 generates a solution to the radiotherapy treatment plan optimization problem based on the estimated one or more optimization variables of the radiotherapy treatment plan optimization problem.

Figure 6:
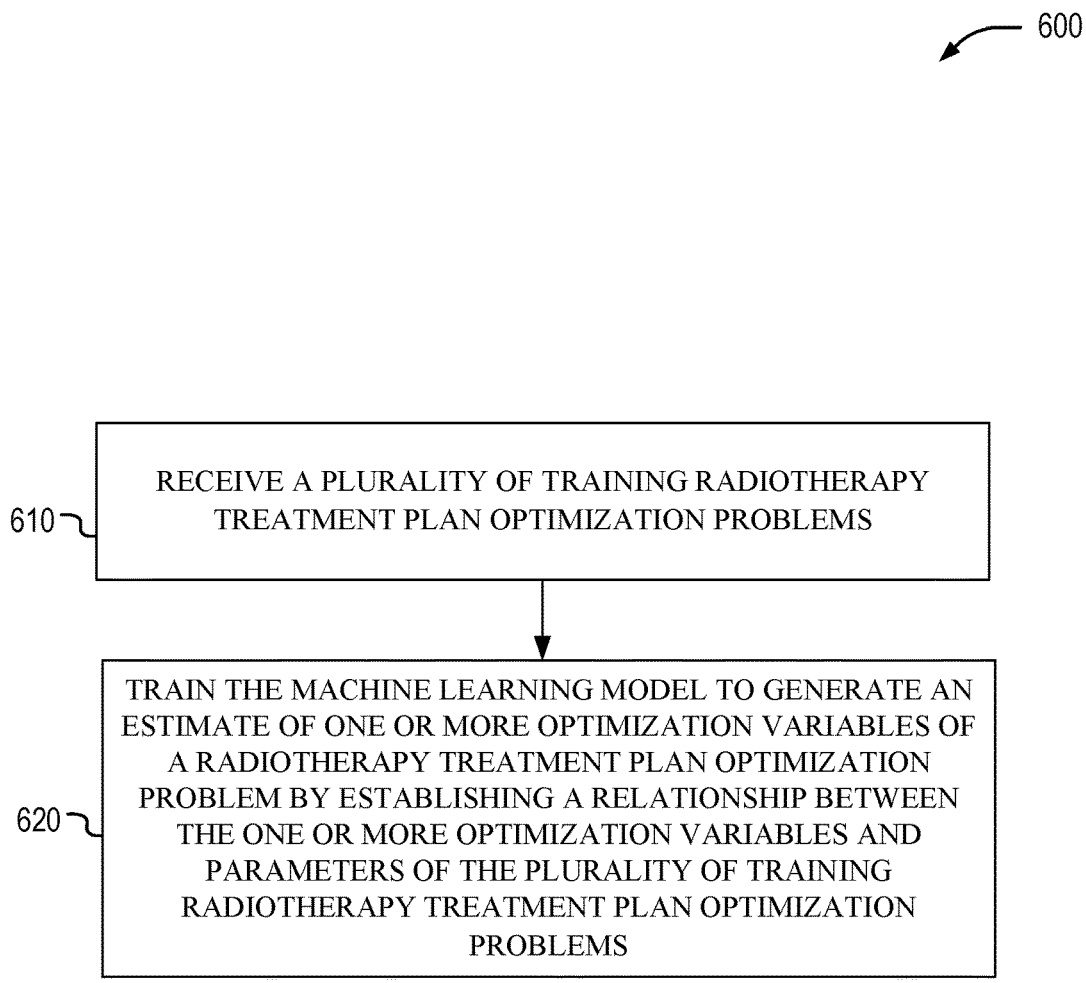

FIG. 6 is a flowchart illustrating example operations of the treatment processing logic 120 in performing a process 600, according to example embodiments. The process 600 may be embodied in computer-readable instructions for execution by one or more processors such that the operations of the process 600 may be performed in part or in whole by the functional components of the treatment processing logic 120; accordingly, the process 600 is described below by way of example with reference thereto. However, in other embodiments, at least some of the operations of the process 600 may be deployed on various other hardware configurations. The process 600 is therefore not intended to be limited to the treatment processing logic 120 and can be implemented in whole, or in part, by any other component. Some or all of the operations of process 600 can be in parallel, out of order, or entirely omitted.

At operation 610, treatment processing logic 120 receives a plurality of training radiotherapy treatment plan optimization problems.

At operation 620, treatment processing logic 120 trains the machine learning model to generate an estimate of one or more optimization variables of a radiotherapy treatment plan optimization problem by establishing a relationship between the one or more optimization variables and parameters of the plurality of training radiotherapy treatment plan optimization problems.

As previously discussed, respective electronic computing systems or devices may implement one or more of the methods or functional operations as discussed herein. In one or more embodiments, the radiotherapy processing computing system 110 may be configured, adapted, or used to control or operate the image-guided radiation therapy device 232, perform or implement the training or prediction operations from FIG. 3, operate the trained treatment model 360, perform or implement the operations of the flowcharts for processes 400-600, or perform any one or more of the other methodologies discussed herein (e.g., as part of treatment processing logic 120). In various embodiments, such electronic computing systems or devices operates as a standalone device or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine-readable medium. While the machine-readable medium may have been described in various examples with reference to be a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present disclosure, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present disclosure also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other beneficial results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matters contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, which when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials, and example parameters, functions, and implementations described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled.

What is claimed is:

1. A method for solving a radiotherapy treatment plan optimization problem, the method comprising:
receiving, by processor circuitry, a radiotherapy treatment plan optimization problem;
classifying the radiotherapy treatment plan optimization problem into a particular type;
generating training data by applying different numbers of iterations of a same particular optimization process to a first training optimization problem to output different solutions to the first training optimization problem, a first set of the training data comprising a first solution of the different solutions resulting from application of the same particular optimization process to the first training optimization problem for a first number of iterations, a second set of the training data comprising a second solution of the different solutions resulting from application of the same particular optimization process to the first training optimization problem for a second number of iterations;
identifying, based on the particular type of the radiotherapy treatment plan optimization problem, a machine learning model of a plurality of machine learning models, the machine learning model trained to solve the particular type of the radiotherapy treatment plan optimization problem that comprises an objective function, a set of decision variables, and a set of constraints, a first of the machine learning models being trained based on the first set of training data, and a second of the machine learning models being trained based on the second set of training data;
processing, by the processor circuitry, the radiotherapy treatment plan optimization problem with the machine learning model to estimate one or more optimization variables of the radiotherapy, treatment plan optimization problem by generating one or more estimated values of the set of decision variables, wherein the machine learning model is trained to establish a relationship between the one or more optimization variables and parameters of a plurality of training radiotherapy treatment plan optimization problems, wherein the machine learning model includes a deep neural network; and
applying a non-learned optimization process to the estimated one or more optimization variables of the radiotherapy treatment plan optimization problem to generate a solution to the radiotherapy treatment plan optimization problem, wherein the solution comprises at least one of radiotherapy device parameters, fluence maps, isocenter locations, beam-angles or beam-on times.

2. The method of claim 1, wherein the machine learning model comprises one or more intermediate estimated optimization variables used in a subsequent iteration of the machine learning model, the first set of training data comprising a synthetically generated radiotherapy treatment plan optimization problem and an intermediate solution to the synthetically generated radiotherapy treatment plan optimization problem.

3. The method of claim 1, wherein processing the radiotherapy treatment plan optimization problem comprises:

processing the radiotherapy treatment plan optimization problem with the machine learning model to estimate one or more initial optimization variables; and
solving the radiotherapy treatment plan optimization problem starting from the one or more initial optimization variables using a different learned or non-learned optimization process.

4. The method of claim 1, wherein the non-learned optimization process includes at least one of a simplex method, an interior point method, a Newton method, a quasi-Newton method, a Gauss-Newton method, a Levenberg-Marquardt method, a linear least-squares method, a gradient descent method, a projected gradient method, a conjugate gradient method, an augmented Lagrangian method, a Nelder-Mead method, a branch and bound method, a cutting plane method, simulated annealing, or sequential quadratic programming.

5. The method of claim 1, wherein the plurality of training radiotherapy treatment plan optimization problems includes at least one of: optimization problems derived from previous radiotherapy treatment plans; or synthetically generated problems.

6. The method of claim 1, wherein the radiotherapy treatment plan optimization problem comprises at least one of images of a patient or patient volume, a segmentation of the patient volume, a dose kernel, a dose volume histogram constraint, or a dose constraint.

7. The method of claim 1, wherein the radiotherapy treatment plan optimization problem is a constrained optimization problem, further comprising:
converting the radiotherapy treatment plan optimization problem to an unconstrained optimization problem based on a merit function; and
processing the converted radiotherapy treatment plan optimization problem with the machine learning model to estimate the one or more optimization variables.

8. The method of claim 1, wherein processing the radiotherapy treatment plan optimization problem with the machine learning model to estimate the one or more optimization variables comprises:
selecting a first subset of constraints of the radiotherapy treatment plan optimization problem;
performing a first iteration of processing the radiotherapy treatment plan optimization problem with the machine learning model to generate a first estimate of the one or more optimization variables based on the selected first subset of the constraints;
selecting a second subset of constraints of the radiotherapy treatment plan optimization problem; and
performing a second iteration of processing the radiotherapy treatment plan optimization problem with the machine learning model to generate a second estimate of the one or more optimization variables based on the selected second subset of the constraints.

9. The method of claim 8 further comprising performing one or more additional iterations comprising selecting subsets of constraints and processing the radiotherapy treatment plan optimization problem with the machine learning model.

10. The method of claim 1, further comprising:
randomly selecting a first set of constraints of the radiotherapy treatment plan optimization problem to solve the radiotherapy treatment plan optimization problem using the machine learning model in a first iteration; and
randomly selecting a second set of constraints of the radiotherapy treatment plan optimization problem to solve the radiotherapy treatment plan optimization problem using the machine learning model in a second iteration subsets of constraints are selected randomly.

11. A method for training a machine learning model to solve a radiotherapy treatment plan optimization problem, the method comprising:
receiving, by processor circuitry, a plurality of training radiotherapy treatment plan optimization problems;
classifying the plurality of training radiotherapy treatment plan optimization problem into particular types;
generating training data by applying different numbers of iterations of a same particular optimization process to a first training optimization problem to output different solutions to the first training optimization problem, a first set of the training data comprising a first solution of the different solutions resulting from application of the same particular optimization process to the first training optimization problem for a first number of iterations, a second set of the training data comprising a second solution of the different solutions resulting from application of the same particular optimization process to the first training optimization problem for a second number of iterations;
identifying, based on the particular type of the radiotherapy treatment plan optimization problem, a machine learning model of a plurality of machine learning models, the machine learning model trained to solve the particular type of the radiotherapy treatment plan optimization problem that comprises an objective function, a set of decision variables, and a set of constraints, a first of the machine learning models being trained based on the first set of training data, and a second of the machine learning models being trained based on the second set of training data; and
training the plurality machine learning models to generate estimates of one or more optimization variables of respective ones of the plurality of training radiotherapy treatment plan optimization problems by establishing a relationship between the one or more optimization variables and parameters of the plurality of training radiotherapy treatment plan optimization problems.

12. The method of claim 11, wherein a first of the plurality of machine learning models is trained in a supervised approach based on a plurality of solutions to the plurality of the training radiotherapy treatment plan optimization problems.

13. The method of claim 12, wherein the first machine learning model is trained in the supervised approach iteratively, in which an intermediate output of one training iteration of the first machine learning model comprising intermediate estimated optimization variables is used in a subsequent training iteration of the first machine learning model.

14. The method of claim 1, wherein the plurality of training radiotherapy treatment plan optimization problems includes constrained optimization problems, further comprising:
converting the plurality of training radiotherapy treatment plan optimization problems to unconstrained optimization problems based on a merit function; and
training a first of the plurality of machine learning models based on the converted radiotherapy treatment plan optimization problems.

15. The method of claim 14, wherein the first machine learning model is trained in an unsupervised approach.

16. A non-transitory computer-readable medium comprising non-transitory computer-readable instructions, the computer-readable instructions comprising instructions for performing operations comprising:
receiving a radiotherapy treatment plan optimization problem;
classifying the radiotherapy treatment plan optimization problem into a particular type;
generating training data by applying different numbers of iterations of a same particular optimization process to a first training optimization problem to output different solutions to the first training optimization problem, a first set of the training data comprising a first solution of the different solutions resulting from application of the same particular optimization process to the first training optimization problem for a first number of iterations, a second set of the training data comprising a second solution of the different solutions resulting from application of the same particular optimization process to the first training optimization problem for a second number of iterations;
identifying, based on the particular type of the radiotherapy treatment plan optimization problem, a machine learning model of a plurality of machine learning models, the machine learning model trained to solve the particular type of the radiotherapy treatment plan optimization problem that comprises an objective function, a set of decision variables, and a set of constraints, a first of the machine learning models being trained based on the first set of training data, and a second of the machine learning models being trained based on the second set of training data;
processing the radiotherapy treatment plan optimization problem with the machine learning model to estimate one or more optimization variables of the radiotherapy treatment plan optimization problem by generating one or more estimated values of the set of decision variables, wherein the machine learning model is trained to establish a relationship between the one or more optimization variables and parameters of a plurality of training radiotherapy treatment plan optimization problems, wherein the machine learning model includes a deep neural network; and
applying a non-learned optimization process to the estimated one or more optimization variables of the radiotherapy treatment plan optimization problem to generate a solution to the radiotherapy treatment plan optimization problem, wherein the solution comprises at least one of radiotherapy device parameters, fluence maps, isocenter locations, beam-angles or beam-on times.

17. The non-transitory computer-readable medium of claim 16, wherein the machine learning model comprises one or more intermediate estimated optimization variables used in a subsequent iteration of the machine learning model.

18. The non-transitory computer-readable medium of claim 17, wherein the radiotherapy treatment plan optimization problem comprises at least one of images of a patient or patient volume, a segmentation of the patient volume, a dose kernel, a dose volume histogram constraint, or a dose constraint, and wherein the solution comprises at least one of radiotherapy device parameters, fluence maps, shot positions, or beam-on times.

19. A system comprising:
a memory for storing instructions; and
one or more processors for executing the instructions stored in the memory for performing operations comprising:

receiving a radiotherapy treatment plan optimization problem;

classifying the radiotherapy treatment plan optimization problem into a particular type;

generating training data by applying different numbers of iterations of a same particular optimization process to a first training optimization problem to output different solutions to the first training optimization problem a first set of the training data comprising a first solution of the different solutions resulting from application of the same particular optimization process to the first training optimization problem for a first number of iterations, a second set of the training data comprising a second solution of the different solutions resulting from application of the same particular optimization process to the first training optimization problem for a second number of iterations;

identifying, based on the particular type of the radiotherapy treatment plan optimization problem, a machine learning model of a plurality of machine learning models, the machine learning model trained to solve the particular type of the radiotherapy treatment plan optimization problem that comprises an objective function, a set of decision variables, and a set of constraints, a first of the machine learning models being trained based on the first set of training data, and a second of the machine learning models being trained based on the second set of training data;

processing the radiotherapy treatment plan optimization problem with the machine learning model to estimate one or more optimization variables of the radiotherapy treatment plan optimization problem by generating one or more estimated values of the set of decision variables, wherein the machine learning model is trained to establish a relationship between the one or more optimization variables and parameters of a plurality of training radiotherapy treatment plan optimization problems, wherein the machine learning model includes a deep neural network; and applying a non-learned optimization process to the estimated one or more optimization variables of the radiotherapy treatment plan optimization problem to generate a solution to the radiotherapy treatment plan optimization problem, wherein the solution comprises at least one of radiotherapy device parameters, fluence maps, isocenter locations, beam-angles or beam-on times.

20. The system of claim 19, wherein the machine learning model comprises one or more intermediate estimated optimization variables used in a subsequent iteration of the machine learning model.

21. The system of claim 19, wherein the radiotherapy treatment plan optimization problem comprises at least one of images of a patient or patient volume, a segmentation of the patient volume, a dose kernel, a dose volume histogram constraint, or a dose constraint, and wherein the solution comprises at least one of radiotherapy device parameters, fluence maps, shot positions, or beam-on times.

* * * * *

UNITED STATES PATENT AND TRADEMARK OFFICE
CERTIFICATE OF CORRECTION

| | |
|---|---|
| PATENT NO. | : 11,605,452 B2 |
| APPLICATION NO. | : 16/512972 |
| DATED | : March 14, 2023 |
| INVENTOR(S) | : Adler et al. |

It is certified that error appears in the above-identified patent and that said Letters Patent is hereby corrected as shown below:

In the Claims

In Column 28, Line 20, in Claim 5, after "of:", insert a linebreak

In Column 28, Line 21, in Claim 5, after "or", insert a linebreak

In Column 31, Line 8, in Claim 19, delete "problem" and insert --problem,-- therefor Signed and Sealed this
Fourth Day of June, 2024

Katherine Kelly Vidal
*Director of the United States Patent and Trademark Office*